(12) United States Patent
Thoret Bauchet (10) Patent No.: US 10,765,964 B2
(45) Date of Patent: Sep. 8, 2020

(54) PROCESS TO MITIGATE UNWANTED FORMATION OF POPCORN POLYMERS USING ACOUSTIC EMISSION SIGNALS

(71) Applicant: TOTAL RESEARCH & TECHNOLOGY FELUY, Seneffe (BE)

(72) Inventor: Jean-Pierre Thoret Bauchet, Bruzelles (BE)

(73) Assignee: Total Research & Technology Feluy, Seneffe (BE)

( * ) Notice: Subject to any disclaimer, the term of this patent is extended or adjusted under 35 U.S.C. 154(b) by 0 days.

(21) Appl. No.: 16/077,001

(22) PCT Filed: Feb. 7, 2017

(86) PCT No.: PCT/EP2017/052586
§ 371 (c)(1),
(2) Date: Aug. 9, 2018

(87) PCT Pub. No.: WO2017/137367
PCT Pub. Date: Aug. 17, 2017

(65) Prior Publication Data
US 2019/0030454 A1   Jan. 31, 2019

(30) Foreign Application Priority Data
Feb. 10, 2016  (EP) .................................. 16154983

(51) Int. Cl.
*B01D 3/42* (2006.01)
*G01N 29/14* (2006.01)
(Continued)

(52) U.S. Cl.
CPC ............... *B01D 3/42* (2013.01); *B01D 3/34* (2013.01); *C07C 7/04* (2013.01); *G01N 29/14* (2013.01);
(Continued)

(58) Field of Classification Search
CPC ... B01D 3/34; B01D 3/42; C07C 7/04; G01N 29/14; G01N 29/42; G01N 29/4427
See application file for complete search history.

(56) References Cited

U.S. PATENT DOCUMENTS 4,734,098 A   3/1988 Wilson
4,754,645 A   7/1988 Piche et al.
(Continued)

FOREIGN PATENT DOCUMENTS

DE    241480 A1    12/1986
GB   2038851 A    7/1980
(Continued)

OTHER PUBLICATIONS

International Search Report issued in PCT/EP2017/052586, dated May 8, 2017, 3 pages.

*Primary Examiner* — Jonathan Miller
(74) *Attorney, Agent, or Firm* — Albert Shung (57) ABSTRACT

Process to monitor unwanted formation of a polymer, having internal mechanical strain, wherein said formation of polymer generates acoustic emissions due to the sudden break of the polymer, wherein the number of said acoustic emissions increases over time when there is formation of said unwanted polymer formation, wherein said acoustic emissions is detected by a resonant piezo electric transducer having a resonant frequency centred on the second harmonic of said acoustic emission.

14 Claims, 6 Drawing Sheets

(51) Int. Cl.
*G01N 29/42* (2006.01)
*G01N 29/44* (2006.01)
*B01D 3/34* (2006.01)
*C07C 7/04* (2006.01)

(52) U.S. Cl.
CPC ......... *G01N 29/42* (2013.01); *G01N 29/4427* (2013.01); *B01J 2219/00254* (2013.01); *C08F 2400/02* (2013.01); *G01N 2291/0251* (2013.01)

(56) References Cited

U.S. PATENT DOCUMENTS

| | | | |
|---|---|---|---|
| 5,072,064 A | 12/1991 | Sun | |
| 8,459,118 B2* | 6/2013 | Bauchet | G01N 29/032 73/587 |
| 9,222,919 B2* | 12/2015 | Thoret Bauchet | G01N 29/032 |
| 2004/0035218 A1* | 2/2004 | Paulson | G01H 1/00 73/803 |
| 2005/0004413 A1 | 1/2005 | Kanauchi et al. | |
| 2007/0060721 A1 | 3/2007 | Muhle et al. | |

FOREIGN PATENT DOCUMENTS

| | | | |
|---|---|---|---|
| WO | 03051929 A1 | 6/2003 | |
| WO | 2008084045 A1 | 7/2008 | |

\* cited by examiner

PROCESS TO MITIGATE UNWANTED FORMATION OF POPCORN POLYMERS USING ACOUSTIC EMISSION SIGNALS

CROSS-REFERENCE TO RELATED APPLICATIONS

This application claims the benefit of PCT/EP2017/052586 filed Feb. 7, 2017, which claims priority from EP 16154983.7 filed Feb. 10, 2016, which are incorporated herein by reference in their entireties for all purposes.

FIELD OF THE INVENTION

The invention relates to a method and apparatus of monitoring the unwanted formation polymers being preferably polymers of 1,3-butadiene also called "popcorn". In particular, the invention relates to an improved method of evidencing and mitigating the popcorn formation.

BACKGROUND OF THE INVENTION

Conjugated diene, such as 1,3-butadiene, isoprene and chloroprene as unsaturated hydrocarbons, are liable to accidentally generate porous insoluble polymer, known as popcorn polymer, both in liquid and gas phases. This is particularly the case in industrial distillation that satisfies various conditions liable to generate the popcorn polymer, such as suitable temperature at operation, high purity monomer, and coexistence of gas and liquid phases, moisture ingredient, and existence of iron rust.

Popcorn polymerization can result from the action of a variety of factors on the concerned monomer, for example oxygen, heat and rust as well as popcorn polymer particles already present in the monomer, which catalyze popcorn polymer formation. Specifically, it appears that the presence of one or more initiators e.g. water, oxygen, or hydrogen peroxide, results in the formation of popcorn polymer "seeds" in the organic material. The seeds themselves then perpetuate polymerization, without further requiring an initiator and/or a cross linking agent; they serve as sites for further polymerization. As the particular mechanism, it is believed that monomer diffuses through the surface of the growing polymer mass, and is added to the polymer at the centre thereof. For this reason, such polymerization is referred to as occurring "from the inside out". Consequently, there is continued incorporation of monomer into the polymer phase, leading to build-up of the popcorn polymer. This continuous incorporation of monomer, added with the cross linking, implies high internal mechanical strains. These strains explain why the polymers breaks, producing new popcorn polymer seeds. The result is a hard polymeric foulant, which can cause serious equipment and safety concerns if left unchecked.

A particular problem attendant upon popcorn polymer formation is its extreme resistance to deactivation, once present in a system. Some of the seeds become attached to the processing and handling equipment, and cannot be readily removed by mechanical means; moreover, being insoluble in most common solvents, they are virtually impossible to wash out by use of such solvents. Even after equipment and storage facilities have been cleaned thoroughly, residual particles of popcorn polymer remain, and promote unwanted polymer growth. Trace particles remaining in the equipment will stay active for long periods without the presence of monomer, and serve to initiate polymerization when once again contacted therewith.

Popcorn polymer formation is especially critical in the case of conjugated diene monomers, such as 1,3-butadiene or isoprene. Here, popcorn polymerization may be responsible for pipe work and reactors becoming plugged and for tank charges polymerizing wholesale and the tanks concerned bursting as a consequence.

PRIOR ART DESCRIPTION

GB 2038851 relates to a method of, and an apparatus for, continuously measuring the polymerisation process of vinyl chloride and other monomers, using acoustic principles. An acoustic transducer located in polymerising medium responds to acoustical energy emission from chemical and physical interactions in the polymerisation medium. The transduced signal is acoustically coupled via a scanning sound wave-guide and the resulting electrical signal is relayed to a spectrum analyser which provides an indication of a particular polymerisation process by comparison with a model polymerization having the desired parameters. The waveguide and sensor are located in the polymerisation medium.

DD 241480 relates to the follow up of emulsion polymerization of vinylacetate polymers. This polymerization generates acoustic emission recorded by transducers of the basic frequency in the range of 100 kHz to 1 MHz. This document clearly indicates that the acoustic emission is only generated during the particle formation in the presence of powder initiator. The acoustic emission is not generated by the polymer itself.

WO 03/051929 relates to the follow up of a fluidized polyethylene polymerization reactor. Such follow up is performed via acoustic measurement and comparison of the obtained signal with the signal of a control reactor.

US 2007/0060721 describes the control of polymer stickiness in a gas phase polymerization reactor. The concerned monomers are ethylene and alpha olefins. This document clearly states that the stickiness follow up is monitored via the decrease of the acoustic emission and the comparison is made with reference to a steady state reactor. The followed signal is centred at a frequency of 190 kHz. This document gives no applicable teaching for avoiding the popcorn formation.

US 2005/0004413 teaches a method for limiting the formation of popcorns via injection of polymerization inhibitor. The follow up of popcorn formation is performed by measuring the consumption of polymerization inhibitor.

U.S. Pat. No. 4,734,098 describes the use of a thickness-shear mode resonator placed inside the stream to simultaneously measure mass deposition and fluid properties. According to this document the resonator would be sensitive to the formation of viscoelastic polymer (popcorns) in the vapour phase which would deposit on the resonator. This resonator would allow following the formation of popcorns and it would allow delivering the exact amount of antifoulant. However the disclosure of this application is not supported by examples. It is expected that fouling and deposition on the resonator can find its origin on other components like the cooling water for instance.

U.S. Pat. No. 5,072,064 describes inhibitors of popcorn polymer containing compound of group IV element and at least one hydrogen bonded to the Group IV element.

U.S. Pat. No. 4,754,645 describes a method for ultrasonically characterizing polymer materials under simulated processing conditions.

WO 2008/084045 discloses the possibility of following the popcorn emission via measurement of an acoustic emission. This document discloses that during the formation of popcorn, acoustic shots are produced. This document also discloses that the acoustic shots can be followed.

However, this document gives only a general teaching about the acoustic emissions produced by the popcorns. In particular, this document is silent on the problems encountered with the industrial noises surrounding the acoustic sensor. This document is also silent on how to improve the signal over noise ratio. Indeed an improved signal over noise ratio is of a great importance to be able to detect the remote formation of popcorn.

There is therefore a need for a process to mitigate the unwanted popcorn formation of a cross-linked polymer with an improved method of detection of popcorn polymers and/or that allows intervening on the installation in order to limit the unwanted popcorn formation of a cross-linked polymer more rapidly.

BRIEF DESCRIPTION

The invention relates to a process to mitigate the unwanted popcorn formation of a cross-linked polymer having internal mechanical strain comprising the steps of:

a) providing an installation in which unwanted popcorn formation of a cross-linked polymer may occur, with at least one resonant piezo electric transducer being attached outside of said installation (in contact with said installation so that said acoustic emission can be transmitted to said resonant piezo electric transducer with low signal losses);

b) counting the acoustic emissions generated by said cross-linked polymer formation originating by the sudden break of the polymer with said at least one resonant piezo electric transducer and comparing the number of acoustic emissions counted per unit of time with at least one predefined threshold; and c) intervening on said installation in order to limit the unwanted popcorn formation of a cross-linked polymer when the number of acoustic emissions counted per unit of time of step b) is higher than said at least one predefined threshold;

remarkable in that the step of counting the acoustic emissions is done by detecting the second harmonic of said acoustic emissions.

The unwanted popcorn formation is an unwanted formation of a polymer, having internal mechanical strain, wherein said formation of polymer generates acoustic emissions due to the sudden break of the polymer, wherein the number of said acoustic emissions increases over time when there is formation of said unwanted polymer formation being preferably 1,3-butandiene popcorn polymer. It shall be understood that resonant piezo electric transducer having a resonant frequency centred on the second harmonic of said acoustic emission is equivalent to a resonant piezo electric transducer having its maximum sensitivity or maximum frequency response in the range of the second harmonic of said acoustic emission.

It has been evidenced that the invention is particularly efficient with cross linked polymers. Indeed such polymers emit the strongest acoustic emission. Therefore such emissions are more easily detected by the resonant piezo electric transducer.

It has been discovered that the industrial noise of the installation falls very close to the main frequency of the acoustic emissions. Indeed the industrial noise falls in the range of 50 kHz probably because it is the frequency of the rotating equipments generally used. The first harmonic (or fundamental tone) of the acoustic emission being in the range of 70 to 90 kHz, measuring the fundamental frequency of acoustic emissions being in this range, leads to a poor signal over noise response. However the intensity of the industrial noise of the installation decreases rapidly. When the second harmonic of the acoustic emission is monitored, the intensity of the industrial noise has strongly decreased while the intensity of the second harmonic is still high enough to perform a measurement with a correct signal over noise ratio.

In a particular embodiment, the process object of the present invention comprises the measurement of the acoustic emissions emitted when there is unwanted formation of polymer and that it is preferably the increase of the number of said acoustic emissions counted per unit of time that is monitored and compared with a threshold or the total counts of the acoustic emissions in comparison with a reference or a threshold.

The process is further remarkable in that said acoustic emission is due to the sudden break of the polymer said acoustic emission having preferably its first harmonic (or fundamental tone) in the range of 70 to 90 kHz and its second harmonic centred in the range of 140 to 180 kHz. The process is further remarkable in that said resonant piezo electric transducer measures the second harmonic of said acoustic emissions being preferably in the range of 140 to 180 kHz.

The process is further remarkable in that the resonant frequency (V/μbar, calibration based on ASTM E976) of said resonant piezo electric transducer is in the range of 140 to 180 kHz i.e. in the range of the second harmonic of said acoustic emissions.

It has been indeed discovered that the first harmonic (or fundamental tone) of the acoustic emission is at about 80 kHz. Additionally it has been discovered that the second harmonic of the acoustic emissions has a frequency at about 160 kHz. Advantageously said resonant piezo electric transducer has a maximum sensitivity or its resonant frequency in the range of the second harmonic of the acoustic emission so that it acts as an independent filter.

The process is further remarkable in that said resonant piezo electric transducer is attached outside of a piece of equipment. There is no need to place the resonant piezo electric transducer inside the installation hence avoiding problems of leaking, depressurisation or pollution of the installation. Indeed the acoustic emissions measured are able to pass through the installation walls.

The process is further remarkable in that the step b) of counting the acoustic emissions includes filtering and amplifying the signal obtained by said resonant piezo electric transducer during the measurement of said acoustic emissions.

It has been discovered that counting the acoustic emissions and normalizing the counts obtained over a period of time allows having a relevant parameter characterizing the formation of unwanted polymer. The monitoring of this parameter allows evidencing the presence of unwanted polymer as well as characterizing the formation intensity. When the said parameter is almost zero, there is no formation of unwanted polymers. When the parameter is of at least equal to the reference or to a given threshold, it can be deduced that there is formation of unwanted polymer. When said normalized count is increasing, it can be deduced that the formation of said unwanted polymer is increasing and that actions should be taken like for instance said step c) of intervening on said installation.

The invention is also further remarkable in that said normalization of the counts over time is performed over a time period of one hour.

It was evidenced that the normalization of the counts over time is adequately performed over one hour. Choosing one hour for normalizing the parameter allows having a value easily interpretable. The measurement of the counts before normalizing is usually performed over a shorter period of time. Unwanted formation of polymer can be measured in period of times in the range of 5 minutes, preferably 10 minutes even more preferably in the range of 20 minutes. In those case, normalizing the counts consists in multiplying the counts obtained during 5, 10 or 20 minutes by respectively 12, 6 and 3 to obtain a normalized count over one hour.

The process is also further remarkable in that said resonant piezo electric transducer has an operating frequency range of at least more than two times the frequency of said second harmonic or has a operating frequency range from 1 to 450 kHz preferably from 50 to 400 kHz. Indeed to avoid having parasitic signals, it has been evidenced that the range of frequency measurement of said resonant piezo electric transducer cannot be in the range of a multiple of two of the main frequency but has to be of a wider range than two.

The process is also further remarkable in that it further comprises the steps performed after step a) of:

a1) attaching said at least one resonant piezo electric transducer outside said installation a2) checking the coupling of said installation with said at least one resonant piezo electric transducer. Checking the coupling of the installation with said at least one resonant piezo electric transducer consists in verifying that the acoustic emissions are correctly transferred from the wall of said installation to the resonant piezo electric transducer. This checking can be done by any known method in the art. One possible way is to provide and acoustic emission device that is put in contact with the wall of the installation, to emit acoustic emission at a frequency in the range of 140 to 180 kHz with the help of the acoustic emission device and to check that said piezo electric transducer also placed in contact with the wall of the installation receives correctly the acoustic emission generated by the acoustic emission device.

In another embodiment, said resonant piezo electric transducer is in the form of a portative device. In this case, said resonant piezo electric transducer is non-permanently attached to the piece of equipment to be checked. Such device can be placed advantageously on the unit where unwanted polymer formation is suspected. Advantageously various installation of a given plant can be checked with one portative device equipped with at least one resonant piezo electric transducer.

The process is also further remarkable in that said step c) of intervening on said installation includes:

Injecting at least one additive able to limit the formation of unwanted popcorn or Isolating and washing the part of the installation where unwanted popcorn formation was detected or removing the unwanted popcorn present or Stopping said installation in order to mechanically or manually remove or washing the unwanted popcorn Locating on said installation where the number of said acoustic emission is the maximum and nearby injecting at least one additive able to limit the formation of unwanted popcorn polymers.

The process is further remarkable in that said additives able to limit unwanted popcorn formation of a cross-linked polymer is chosen among compounds having 2,2,6,6-tetramethylpiperidine group being preferably at a concentration of 1 to 5 wt ppm; or phenolic stabilizer being preferably at a concentration of 200 to 1000 wt ppm; or group of molecules being hydroxylamine compounds being preferably at a concentration of 50 to 500 wt ppm; or di-lower akylhydroxylamine or are preferably:

4OH tempo, i.e. 4-Hydroxy-2,2,6,6-tetramethylpiperidine 1-oxyl, being at a concentration of 1 to 5 wt ppm or TBC, i.e. 4-tert-Butylcatechol, being at a concentration of 200 to 1000 wt ppm or di ethyl hydroxylamine being at a concentration of 50 to 500 wt ppm or any combination of thereof and wherein said concentration is based on the total weight of the stream in which said unwanted popcorn formation of cross-linked polymer may occur and is measured at the point of injection of said additive.

It shall be clear that the concentration of additive represents mainly the concentration of said additive in the feed stream to be treated at the point of injection. In addition, the additive being consumed the concentration given represents the concentration given at the point of the injection. Measurements performed at other place in the process may indicate lower concentration of additives in the feed stream.

The process is further remarkable in that said resonant piezo electric transducer is preferably permanently attached to said installation and that said counting the acoustic emissions emitted during the unwanted formation of popcorn is performed on a continuous way i.e. without removing said resonant piezo electric transducer from said installation. In a preferred embodiment, it would not depart from the spirit of the invention to install permanently a resonant piezo electric transducer on the wall of the installation and to monitor the acoustic emission provoked by the unwanted popcorn formation in a similar way as other operating parameters such as for instance the pressure or the temperature. In this case, it is possible to finely tune the addition of at least one additive able to limit the formation of unwanted polymers. More precisely, additives may be added until said normalized counts decreases below a reference or a threshold. Additionally in this case, emergency shut-down of the installation can be performed when the formation of unwanted polymer reaches a too high level being for instance a level equals to four times said reference or threshold.

The process is further remarkable in that said unwanted polymer is derived from 1,3 butadiene, isoprene, dimethyl-2,3-buta-1,3-diene, chloroprene, bromoprene, styrene containing impurities, divinylbenzene and styrene containing traces of divinylbenzene being preferably 1,3 butadiene.

The process is further remarkable in that said installation is any installation where one of the following compound is being converted or purified or transported or stored: 1,3-butadiene, isoprene, dimethyl-2,3-buta-1,3-diene, chloroprene, bromoprene, styrene containing impurities, divinylbenzene and styrene containing traces of divinylbenzene; being preferably a purification section including at least one distillation column of preferably 1,3-butandiene.

The process is further remarkable in that said resonant piezo electric transducer is connected to a conditioner unit comprising a filtering means and an operational preamplifier and wherein preferably in said conditioner unit there is at least one adjustable threshold level or a plurality of cascaded threshold levels.

The process is further remarkable in that said injection of at least one additive able to limit the formation of unwanted popcorn polymers is performed when said number of acoustic emissions counted per unit of time reaches said predefined threshold and that said concentration of said at least one additive injected is further increased when said number of acoustic emissions counted per unit of time reaches a second predefined threshold higher than said predefined threshold and that isolating and washing the part of the installation where unwanted popcorn formation was detected or removing the unwanted popcorn present or said stopping said installation in order to mechanically or manually remove or wash the unwanted popcorn is performed when said number of acoustic emissions counted per unit of time reaches a second predefined threshold higher than said first predefined threshold.

The process is further remarkable in that said step b) of counting the acoustic emissions is performed using multiple resonant piezo electric transducers preferably located where unwanted popcorn formation of a cross-linked polymer may occur.

Definitions

A harmonic of a wave is a component frequency of the signal that is an integer multiple of the fundamental frequency, i.e. if the fundamental frequency is f, the harmonics have frequencies 2f, 3f, 4f, . . . etc.

An overtone is any frequency higher than the fundamental. The tight relation between overtones and harmonics may lead to some possible confusion.

The next table summarizes the possible frequency and the possible name used for the fundamental tone or first harmonic of the acoustic emission emitted during the unwanted formation of popcorn polymer.

| Frequency | Order | Name 1 | Name 2 |
|---|---|---|---|
| f = 80 kHz | n = 1 | fundamental tone | 1st harmonic |
| f = 160 kHz | n = 2 | 1st overtone | 2nd harmonic |

The term fundamental harmonic is sometime used instead of first harmonic. However fundamental harmonic or first harmonic are equivalent.

DETAILED DESCRIPTION

As regards to the unwanted popcorn formation, it can also be referred as the unwanted formation of cross-linked polymer having internal mechanical strain, or unwanted popcorn polymer formation, the three expressions being equivalent. Popcorn polymers are known to form from all manner of organic material, particularly olefinically unsaturated monomers, including olefins and diolefins; especially susceptible are the conjugated diolefins, e.g. butadiene and isoprene, and vinyl compounds, e.g. styrenes and acrylates. They are known as popcorn polymers because they resemble popped corn, these polymers are also referred to in the art as sponge polymers, granular polymers, cauliflower-like polymers, nodular polymers, fluffy polymers, proliferous polymers, and crusty polymers. Popcorn polymer has been considered to occur from spontaneous monomer polymerization via a radical polymerization mechanism. It can occur in both liquid phase and vapour phase, and at any stage of use or handling of the monomer, e.g. recovery, separation, manufacturing, purification, storage, etc. High concentrations of monomer are particularly favourable for its formation. In addition formation of popcorn presents the ability of seeding itself. The popcorn polymers formed are generally resinous polymer that are hard, insoluble, infusible, porous and with a granular aspect.

As regards the monomer which polymerize to make polymers having internal mechanical strain mention may be made of vinyl monomers in general, and not only to a single vinyl monomer but also to a mixture of two or more vinyl monomers. Such vinyl monomer may be $\alpha,\beta$-unsaturated carboxylic acids and esters thereof, ethylene, propylene, 1,3-butadiene, isoprene, dimethyl-2,3-buta-1,3-diene, chloroprene, bromoprene, styrene, divinylbenzene, styrene containing traces of divinylbenzene, vinyltoluene, vinyl chloride and the like. $\alpha,\beta$-unsaturated carboxylic acids and esters thereof include, for example, acrylic acid, methyl acrylate, ethyl acrylate, n-butyl acrylate, i-butyl acrylate, stearyl acrylate, 2-ethylhexyl acrylate, 2-hydroxyethyl acrylate, 2-hydroxypropyl acrylate, 4-hydroxybutyl acrylate, ethylene glycol diacrylate, glycidyl acrylate, 2-ethoxyethyl acrylate, tetrahydrofurfuryl acrylate, cyclohexyl acrylate, benzyl acrylate, allyl acrylate, t-butyl acrylate, 1,6-hexanediol diacrylate, dimethylaminoethyl acrylate, methacrylic acid, methyl methacrylate, ethyl methacrylate, n-butyl methacrylate, i-butyl methacrylate, stearyl methacrylate, 2-ethylhexyl methacrylate, 2-hydroxyethyl methacrylate, 2-hydroxypropyl methacrylate, ethylene glycol dimethacrylate, glycidyl methacrylate, 2-ethoxyethyl methacrylate, cyclohexyl methacrylate, benzyl methacrylate, allyl methacrylate, t-butyl methacrylate, dimethylaminoethyl methacrylate, phenyl methacrylate, crotonic acid, methyl crotonate, ethyl crotonate, itaconic acid, dimethyl itaconate, methyl $\alpha$-hydroxyethylacrylate, ethyl $\alpha$-hydroxyethylacrylate. Mention may be made also of ketones such as methyl vinyl ketone, and nitriles such as acrylonitrile. It is a matter of course that the present invention is not limited thereto.

In a particular embodiment the present invention relates to the above monomers leading to cross-linked polymers. In a more particular embodiment the present invention relates to the above monomers leading to popcorn polymers. By way of example said monomers leading to popcorn polymers are 1,3-butadiene, isoprene, dimethyl-2,3-buta-1,3-diene, chloroprene, bromoprene, styrene containing impurities, divinylbenzene and styrene containing traces of divinylbenzene.

As regards to the acoustic emissions emitted during the unwanted formation of popcorn, this acoustic emissions is generated by the sudden break of the popcorn polymer, it originates from the formation of the unwanted popcorn polymer itself. Indeed the continuous incorporation of monomer in the popcorn polymer, added to the cross linking, implies high internal mechanical strains. These strains explain why the popcorn polymers break, producing new popcorn polymer seeds. The sudden break of the popcorn polymer produces shots in the polymer and on the metallic structure of the equipment. The first harmonic of the acoustic emission produced by the sudden break of the popcorn polymer has a frequency of preferably about 80 kHz+/−10% and the second harmonic has a frequency of preferably about 160 kHz+/−10%. The invention uses this specific property of the popcorn polymer with internal mechanical strain in order to measure the activity of said polymer taking into account the properties of the acoustic emission itself and taking into account the industrial noise surrounding the installations. Acoustic emission is generally defined as the phenomenon of radiation of acoustic (elastic) waves in solids that occurs when a material undergoes irreversible changes in its internal structure. It is also sometimes defined as transient elastic waves within a material, caused by the rapid release of localized stress energy. In our case, the acoustic emissions emitted by the popcorn polymer are transferred through the surrounding environment up to the installation itself and through its walls. The resonant piezo electric transducer located outside the installation is then able to measure the $2^{nd}$ harmonic of the acoustic emission.

As regards to the resonant piezo electric transducer, it can be of any type as long as it can detect the second harmonic of said acoustic emission to be measured, said second harmonic being preferably centred in the range of 140 to 180 kHz. Advantageously said resonant piezo electric transducer has its resonant frequency in the range of the second harmonic of said acoustic emission. Additionally said resonant piezo electric transducer may act as a filter in the range of the main frequency of the acoustic emission. This particular behaviour allows filtering the main frequency of the acoustic emission together with most of the signal induced by the industrial noises. There is therefore a particular advantage in using such resonant piezo electric transducer with a resonant frequency in the range of the second harmonic of the acoustic emission: it allows measuring the second harmonic with sufficient energy to have a significant signal and it allows also filtering the industrial noise present around the main frequency of the acoustic emission. The ratio signal over noise is therefore improved. The resonant piezo electric transducer can be attached by any means to the piece of equipment, by way of example by a magnet. By way of none limiting example resonant piezo electric transducer type R15 or R15a from PAC can be used. They have been particularly successful when used on manholes in a butadiene plant. In order to choose a resonant piezo electric transducer, the man skilled in the art can test various resonant piezo electric transducers having different resonant frequencies. He can then choose the resonant piezo electric transducer having the best signal over noise ratio. Alternatively, he can start with a resonant piezo electric transducer having a resonant frequency in the range of 140 to 180 kHz and compare the signal over noise ratio obtained with other resonant piezo electric transducer having resonant frequencies in other ranges. The choice of the best resonant piezo electric transducer is determined by the best signal over noise response of the resonant piezo electric transducer while measuring the acoustic emissions generated by said cross-linked polymer formation.

As regards to the steps of filtering and amplifying the signal obtained by said resonant piezo electric transducer during the measurement of said acoustic emissions, it consists in any usual techniques related to the treatment of signal. Advantageously the above signal is connected to means to display the frequency, the energy level (can be measured in Decibels (dB)) and amplitude. In a specific embodiment the capture threshold ranges from 30 to 70 dB and is advantageously around 50 dB. In a specific embodiment all these acoustic sensors are connected to means for filtering in order to discriminate against usual noise of said equipment and connected to means to display for each resonant piezo electric transducer the frequency, the energy level and amplitude. Once said signal reaches a given threshold, one additional acoustic emission is counted. Advantageously, the number of counts as function of time is displayed or the normalized counts or both are displayed. Such monitoring of the counts is advantageously done by a computer. In a preferred embodiment said computer sets an alarm in the control room of the plant once the reference or threshold is reached, thus operators know that unwanted polymers are under formation and can decide to reduce capacity and/or to clean said piece of equipment in which said unwanted polymers are present and/or to add said at least on additive able to limit the formation of unwanted popcorn polymers. The choice of the action to take is mainly dependant on the installation itself and based on the know-how of the operator of said installation.

As regards to comparing the number of acoustic emissions counted per unit of time with at least on predefined threshold, it refers to counting the acoustic emissions during a given period of time followed by a conversion to normalize the period of time with a given and constant period of time. In a preferred embodiment the normalized period of time is of one hour. Comparison with a threshold can be performed on normalized counts or counts that were not normalized (hereafter written simply counts). It consists of setting at least one alarm when said counts or normalized counts reach said predefined threshold. It would not depart of the spirit of the invention to set two or three alarms or more when the count reaches a second or a third threshold value being for instance a multiple value of said predefined threshold or reference (for instance the predefined threshold being at 500 counts per hour and the second threshold being three times higher at 1500 counts per hours). The advantage of having more than one threshold is to indicate the operator of said installation the various levels of risk of the formation of unwanted popcorn polymer. For instance, a predefined threshold being determined on the specific installation (having for instance an arbitrary value of 100 counts per hour) would indicate that there is formation of unwanted popcorn polymer. A second threshold determined on the specific installation (having for instance an arbitrary value of 250 counts per hour) would be an indication that the formation of unwanted popcorn polymer is significant. It may for instance be linked with the possibility of injecting one or more additives able to limit the formation of unwanted polymers at a low concentration. For instance, additives able to limit the formation of unwanted polymers are chosen among compounds having 2,2,6,6-tetramethylpiperidine group at a concentration of 1 to 50 wt ppm preferably 1 to 5 wt ppm, for instance being a 4OH TEMPO; or phenolic stabilizer at a concentration of 100 to 2000 wt ppm or preferably 200 to 1000 wt ppm; or group of molecules being hydroxylamine compounds at a concentration of 20 to 1000 wt ppm or preferably 50 to 500 wt ppm; or di-lower akylhydroxylamine, or any combination of thereof. For instance the additives that may be used include 4OH tempo, i.e. 4-Hydroxy-2,2,6,6-tetramethylpiperidine 1-oxyl, being present in said installation at a concentration of 1 to 5 wt ppm or TBC, i.e. 4-tert-Butylcatechol, being present in said installation at a concentration of 200 to 1000 wt ppm or di ethyl hydroxylamine being present in said installation at a concentration of 50 to 500 wt ppm or any combination of thereof. The concentrations of said additives are based on weight of a hydrocarbon mixture including the monomer leading to unwanted polymers and are measured at the point of injection of said additive. A third threshold (chosen for instance at the arbitrary value of 500 counts per hour) would be an indication that the installation requires a strong injection of additives able to limit the formation of unwanted polymers. For instance the additives that may be used include 4OH tempo, i.e. 4-Hydroxy-2,2,6,6-tetramethylpiperidine 1-oxyl, being present in said installation at a concentration of 10 to 20 wt ppm or TBC, i.e. 4-tert-Butylcatechol, being present in said installation at a concentration of 1000 to 5000 wt ppm or di ethyl hydroxylamine being present in said installation at a concentration of 500 to 1000 wt ppm or any combination of thereof. The concentrations of said additives are based on weight of a hydrocarbon mixture including the monomer leading to unwanted polymers and are measured at the point of injection of said additive. In another embodiment this third threshold can also be linked with an alarm indicating that the unit should be shut down and washed as soon as possible. Values for the thresholds are dependent on the type of installation to monitor. Determination of a threshold should be done on site with a measurement campaigns to get the typical values of the installation when there is only little unwanted popcorn formed and when there is a lot of unwanted popcorn formed. It is then from the competency of the man skilled in the art to choose the threshold value based on its knowledge of the installation. Alternatively said predefined threshold may be arbitrary fixed. Then if it appears that it is too low and not representative, it can be adapted depending on the conditions of the installation.

As regards to monitoring the increase of the number of acoustic emissions counted per unit of time, it can be performed on normalized counts or counts. It consists in measuring the counts with time and with modification of the process condition. Indeed, for each installation, the formation of unwanted polymer may be associated with dedicated operating conditions or with the treatment of particular feed stream. Follow up of the variation of the counts with the various operating condition would allow a better understanding of the conditions leading to unwanted polymer formation. It would therefore not depart from the spirit of the invention to adapt the operating conditions while monitoring the acoustic emission generated by said unwanted popcorn formation.

As regards to predefined threshold or reference, it can consist in normalized count value associated with the formation of unwanted polymer. For instance, it can consist in any discrete value between 10 and 1 000 000 counts per hour. The terms reference and predefined threshold are equivalent. It can be firstly an arbitrary value based on the experience of the man skilled in the art. This value can then be adapted depending on the installation and on the experience gained. Usually a low value is given for the predefined threshold and it is then increased when it appears to be too low. On the contrary it can be decreased if it appears that the value for the predefined threshold is too high. Such adaptation is a usual skill of the man of the art.

As regards to the step of checking of the coupling of said piece of equipment with said resonant piezo electric transducer, it consists in the verification of the transmission of the acoustic emission from the installation to the resonant piezo electric transducer. It can consist for example in using an artificial source of acoustic emission fixed on the installation sufficiently far from said resonant piezo electric transducer in order to check that there is a good transmission of the acoustic emission as it is known in the art.

According to another embodiment, the invention also includes localizing the place where unwanted polymer formation takes place; it can consist in measuring the formation of unwanted polymer at various place of the installation and thereby determining the place where the number of acoustic emission is the higher. It can either consist in using more than one resonant piezo electric transducers to measure the acoustic emission in well defined places of the installation followed by a calculation or simulation of the origin of the source of the acoustic emission as it is known in the art.

As regards to the additives able to limit the formation of unwanted popcorn polymers, they are sometimes also named polymerization inhibitors. The two terms are strictly equivalent. Such additives which can be used in the present invention are used for suppressing generation of unwanted popcorn polymer inside the apparatus. Any type of additives suitable for limiting the formation of unwanted popcorn polymer can be used.

More precisely, as to inhibit and suppress unwanted polymerization by scavenging radicals with stable radicals, 1,1-diphenyl-2-picrylhydrazyl, 1,3,5-triphenyl ferudazyl, 2,6-di-t-butyl-a-(3,5-di-t-butyl-4-oxo-2,5-cyclohexanediene-lindene)-p-tolyloxy, 2,2,6,6-tetramethyl-4-piperidoneloxyl, N-(3-N-oxyanilino-I,3-dimethylbutylidene)-aniline oxide, 2-(2-cyanopropyl)-ferudazyl; as to inhibit and suppress polymerization by chain transfer reaction, ones having activated NH-bond such as diphenylpicrylhydrazine, diphenylamine, diethylhydroxylamine, dimethylhydroxylamine, methylethylhydroxylamine, dipropylhydroxylamine, dibutyhydroxylamine, dipentylhydroxylamine; ones having OH bond of phenol such as hydroquinone and t-butylcatechol; ditiobenzoyldisulfide, p,p'-ditolyl trisulfide, p,p'-ditolyl tetrasulfide, dibenzyl tetrasulfide, tetraethylthiuram disulfide; as to inhibit and suppress polymerization by addition reaction, oxygen, sulfur, anthracene, 1,2-benzanthracene, tetracene; benzoquinone derivatives such as chloranil, p-benzoquinone, 2,6-dichlorbenzoquinone, 2,5-dichlor benzoquinone, nitro compounds such as furfurylidene-malononitrile and m-dinitrobenzene, nitroso compounds such as nitrosobenzene, 2-methyl-2-nitrosopropane; further, metal salts such as ferric chloride and ferric bromide are exemplified.

Out of the above polymerization inhibitors, ones that inhibit and suppress the polymerization by chain transfer reactions, particularly di-lower aklylhydroxylamine is preferable. More precisely, diethylhydroxylamine is preferable. Other preferable compounds include 4OH tempo, i.e. 4-Hydroxy-2,2,6,6-tetramethylpiperidine 1-oxyl, being present in said installation at a concentration of 1 to 5 wt ppm or TBC, i.e. 4-tert-Butylcatechol, being present in said installation at a concentration of 200 to 1000 wt ppm or di ethyl hydroxylamine being present in said installation at a concentration of 50 to 500 wt ppm or any combination of thereof. The concentrations of said additives are based on weight of a hydrocarbon mixture including the monomer leading to unwanted polymers and are measured at the point of injection of the additives. It would not depart from the spirit of the invention to use a combination of two or more additives. A method of using a polymerization inhibitor is not particularly limited and may be attained by simply bringing the monomer leading to unwanted polymer or a hydrocarbon mixture including monomer leading to unwanted polymer in contact with the additive.

As regards to the isolation and removal or washing of the part of the installation where unwanted popcorn formation was detected or removing the unwanted popcorn present, it can consist, when required, in shutting down the whole installation or only a part of it. After then, it can consist in purging the installation and checking the place where unwanted popcorn polymer formation was detected. Afterwards, the unwanted popcorn polymers evidenced in the installation can be removed. Any type of manual or mechanical removal or any type of washing may be suitable. However, it is preferable to manually wash and remove any traces of unwanted popcorn polymer. A rigorous washing of the installation is required in order to suppress any seeds of unwanted popcorn polymer. Indeed, if some traces of unwanted popcorn polymer are left in the installation, they may seed further the formation of unwanted popcorn polymer. Advantageously, with the help of the present invention, the origin of the seeds of unwanted popcorn polymer can be clearly detected which allow concentrating its effort on clearly washing or cleaning this particular part of the installation. The invention therefore allows concentrating the effort of washing the installation where it is the most required and where it can lead to limiting the formation of unwanted popcorn polymer.

EXAMPLES

Example 1 (Comparative)

In this example, the formation of unwanted polymer is evidenced on a heat exchanger in a purification section of a 1,3-butadiene plant i.e. in the distillation column of 1,3-butadiene. The measurement of the acoustic emissions is performed with Doppler vibrometric Laser Polytec. The Doppler laser allows the acquisition of frequencies over a large bandwidth. The acquisition system used ranges from 0 to 20 kHz and is of a type 01 dB. The spectra obtained were acquired on a numeric oscilloscope having acquisition capacity.

Figure 1:
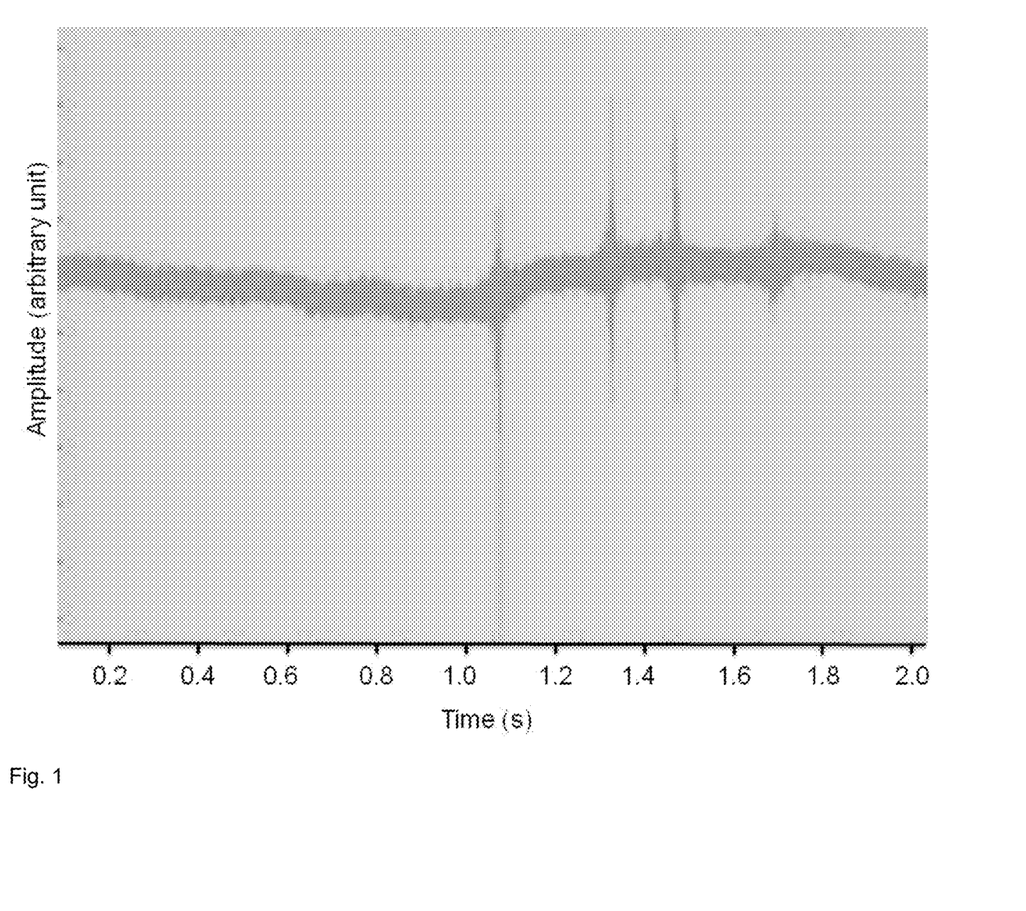
FIG. 1: Raw signal obtained with a Doppler laser on a heat exchanger where 1,3-butadiene pop corn is known to be formed.
Figure 2:
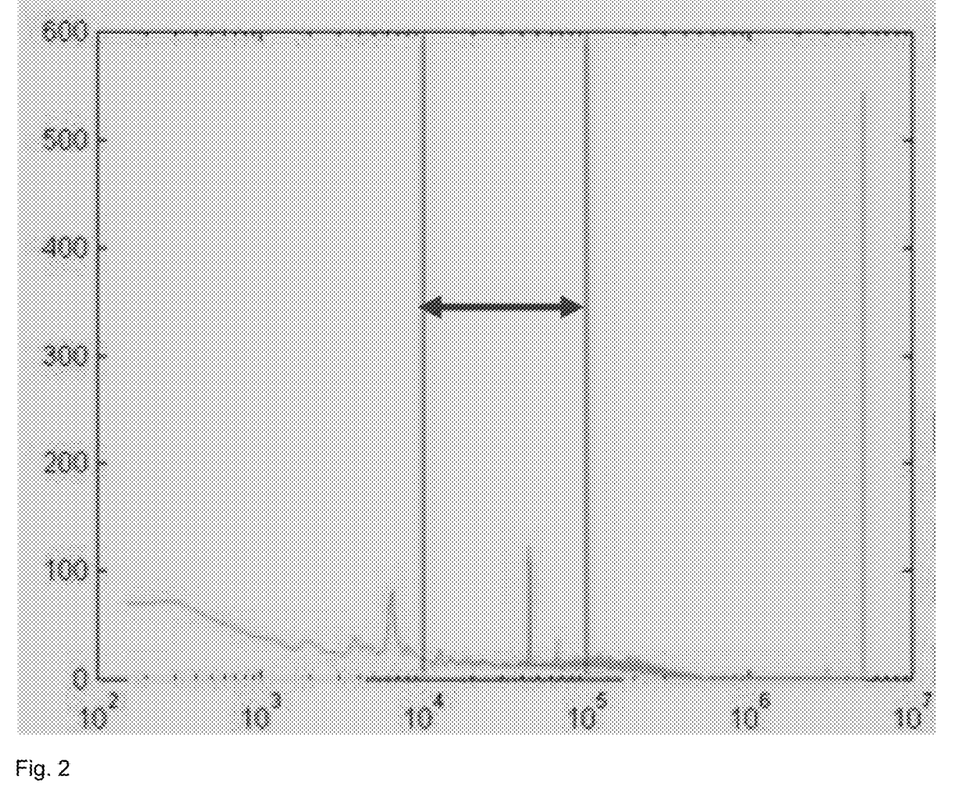
FIG. 2: Spectral analysis of the raw signal of FIG. 1.
Figure 3:
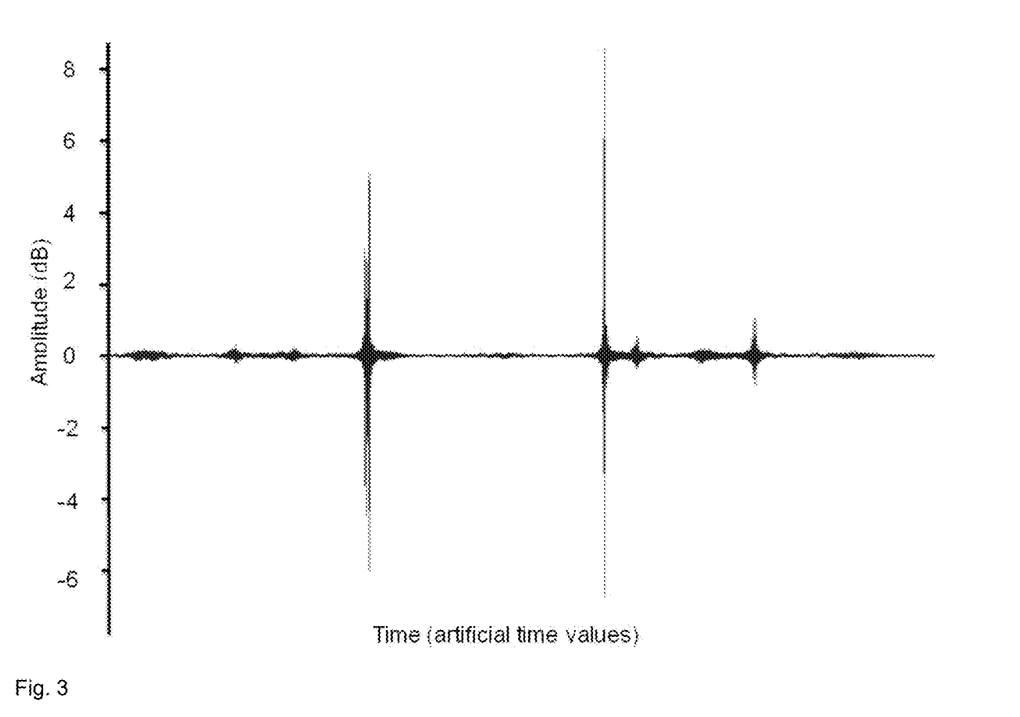
FIG. 3: Signal after filtrating in the range of 10-100 kHz allowing the suppression of noise

The FIG. 1 gives an example of the type of raw signal obtained. The spectral analysis of such signal is given on FIG. 2. The first harmonic of the acoustic emission as well as the second harmonic can be evidenced in the range of 10 to 200 kHz. Once filtered in this range of frequency, the signal obtained is presented on the FIG. 3. It appears from this analysis that the unwanted popcorn acoustic emission has its first harmonic of about 80 kHz. It also appears that the second harmonic has a frequency of about 160 kHz.

Although the bandwidth of the Doppler Laser is very large, it presents the disadvantage of being not sensitive enough to clearly identify the acoustic emission produced by the 1,3-butadiene pop corn polymers. Addition of a filter centred on the first or the second harmonic does not improve the signal over noise ratio because the Doppler Laser is still not sensitive enough.

Example 2 (According to the Invention)

In order to have a correct measurement of the acoustic emission, it is required to improve the signal over noise ratio. Tests were performed using two types of resonant piezo electric transducer. The resonant piezo electric transducer of the type Physical Acoustics (PAC) PAC R15a is placed on channel 1. The R15a has a resonant frequency, V/µbar, at 150 kHz. The second resonant piezo electric transducer of the type Physical Acoustics (PAC) PAC R6a is placed on channel 2. The R6a has a resonant frequency, V/µbar, at 90 kHz. Differentiating the acoustic emissions from the industrial noise was only possible using the resonant piezo electric transducer R15a having its resonant frequency V/µbar at 150 kHz.

It is known that the signal on the second harmonic is less powerful than the first harmonic. So, the first idea would be to use the first harmonic to detect more easily the acoustic emissions. This was done using the resonant piezo electric transducer of R6a type. Surprisingly during the tests performed industrially, it appeared that this is not the best way to do. The resonant piezo electric transducer R6a was indeed saturated with the industrial noise.

Figure 4A:
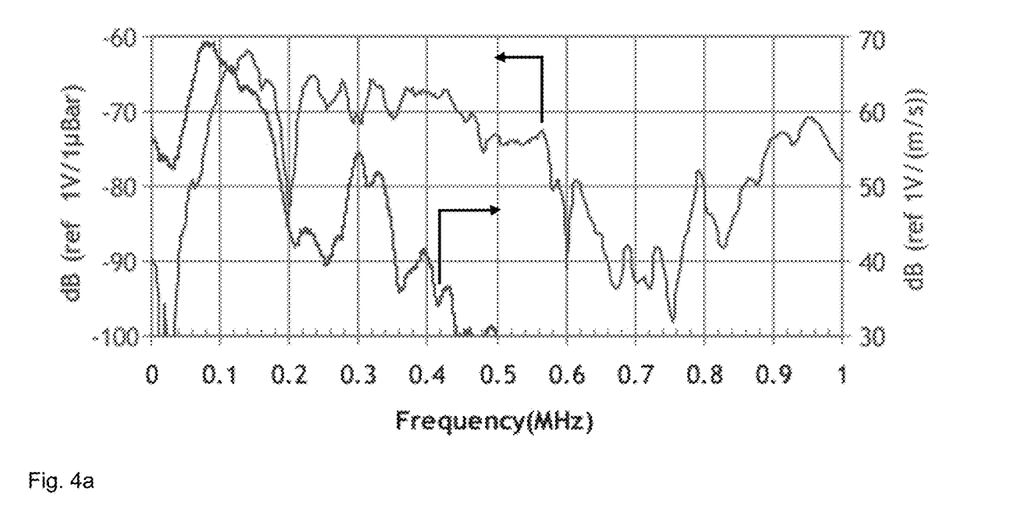
FIG. 4*a*: Frequency response of the resonant piezo electric transducer R15a (1V/(m/s) calibration based on ASTM E1106; 1V/µbar calibration based on ASTM E976)

The two resonant piezo electric transducers were used in parallel and on the same measurement point to check the impact of the choice of the frequency. The characteristics of those resonant piezo electric transducers are summarized in the table below. The different responses in frequency of the two resonant piezo electric transducers are presented on FIGS. 4*a* and 4*b*. FIG. 4*a* indicates that the maximum response in frequency of the piezo electric transducer R15a is in the range of 160 kHz i.e. where the second harmonic is located.

Figure 4B:
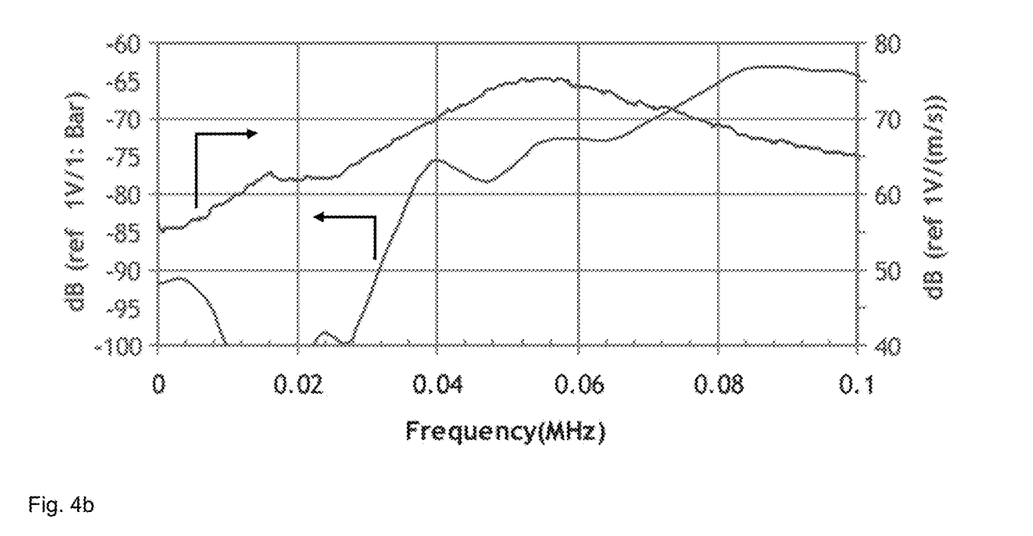
FIG. 4*b*: Frequency response of the resonant piezo electric transducer R6a (1V/(m/s) calibration based on ASTM E1106; 1V/bar calibration based on ASTM E976)

|  | Channel 2 R6a (first harmonic) | Channel 1 R15a (second harmonic) |
|---|---|---|
| Frequency filter (kHz) | 100 | 20 |
| Power filter (dB) | 50 | 50 |

Figure 5:
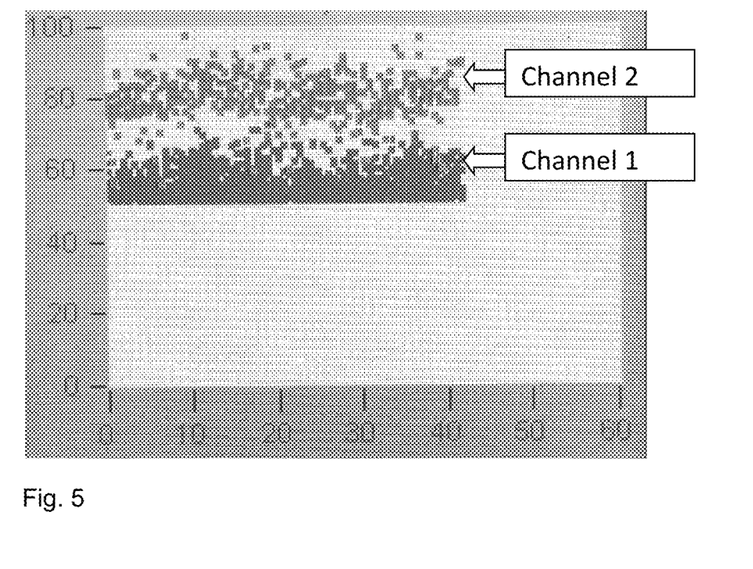
FIG. 5: Amplitude in dB versus time in second of a first piezo electric transducer having a frequency filter of 100 kHz (channel 1-R15a) and a frequency filter of 20 kHz (channel 2-R6a)

It can be seen from FIG. 5 that the channel 2 receives an average of signal 20 dB higher than channel 1. This higher signal response is due to the industrial noise.

Figure 6:
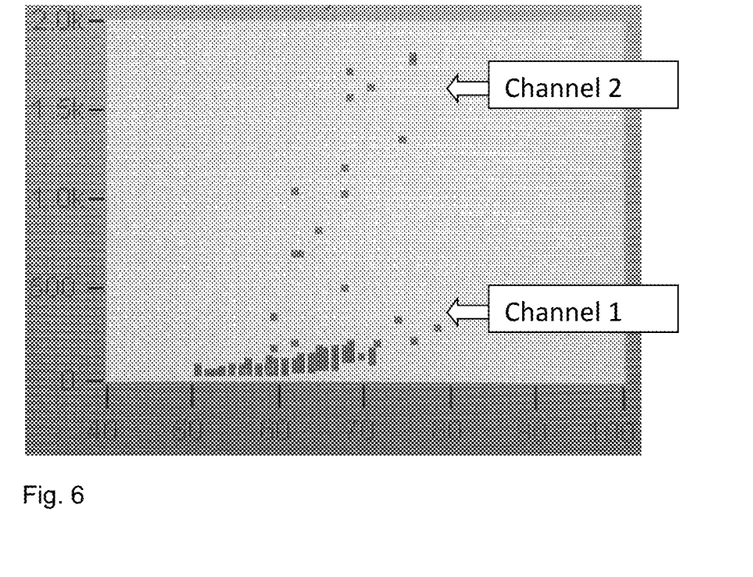
FIG. 6: Energy versus amplitude in dB of a first piezo electric transducer having a frequency filter of 100 kHz (channel 1-R15a) and a frequency filter of 20 kHz (channel 2-R6a)

The FIG. 6 displays the dispersion of the energy of the signal. It appears that the signals energy is more dispersed on channel 2 i.e. it is more dispersed using the resonant piezo electric transducer with the resonant frequency near the first harmonic. The resonant piezo electric transducer is not selective toward the acoustic emissions generated by the unwanted popcorn formation, it responds to all the industrial noise present in the environment.

Figure 7:
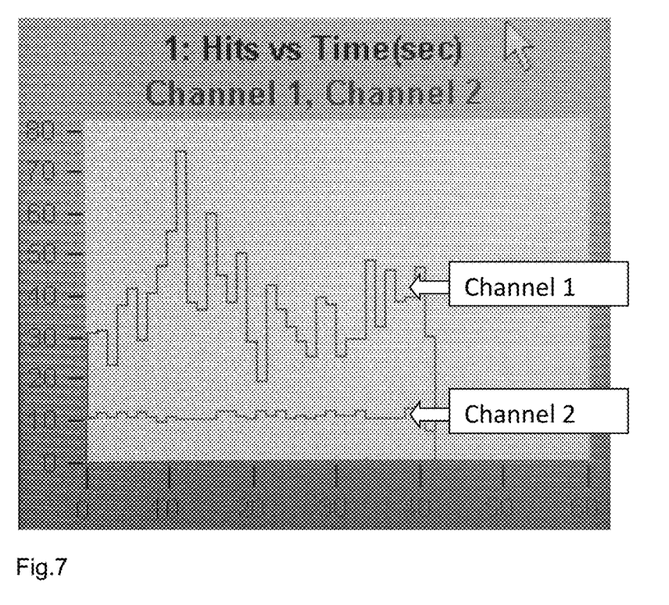
FIG. 7: Number of hits versus time in second of a first piezo electric transducer having a frequency filter of 100 kHz (channel 1-R15a) and a frequency filter of 20 kHz (channel 2-R6a)

The direct consequence is the sensor saturation with signals in the case of channel 2. Consequently the separation of different signals is not as efficient in the case of channel 1. On FIG. 7, it appears that it was impossible to separate and count hits received by sensor of channel 2 whereas it was possible on channel 1.

It consequently appears that the use of a resonant piezo electric sensor having its main frequency in the range of the second harmonic of the acoustic emission allows having an improved signal over noise ratio and therefore it allows reliably counting the acoustic emission.

Figure 8:
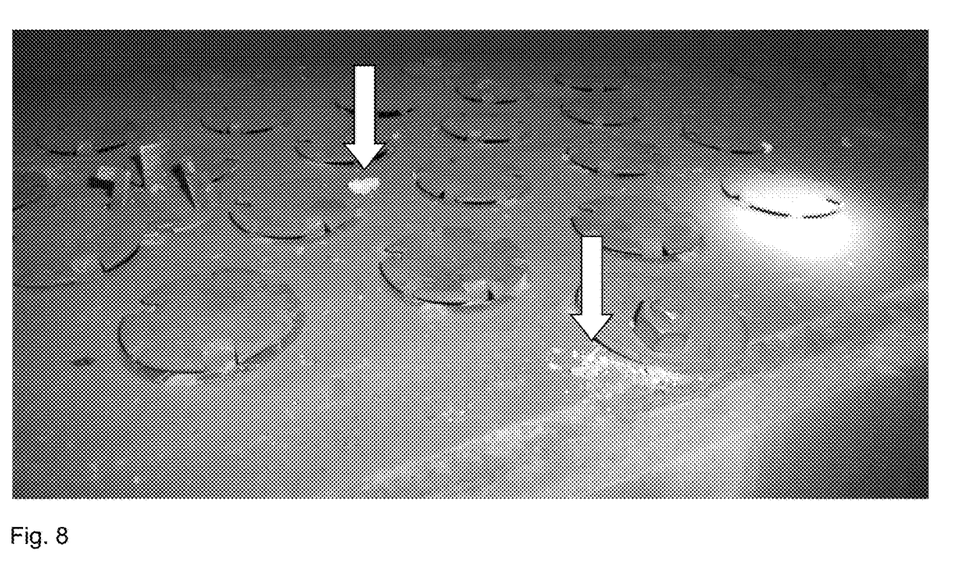
FIG. 8: Picture taken inside a distillation column where 1,3-butadiene pop corn was evidenced (see under the arrows).

The distillation column was afterwards stopped, purged and opened. The FIG. 8 shows a picture of the distillation trays where pop corns were found. The unwanted popcorn was removed and distillation column was washed. The measurements performed using the resonant piezo electric transducer therefore clearly allow evidencing the formation of pop corn polymer of 1,3-butadiene so that intervening on the distillation column was possible.

The invention claimed is:

1. A process to mitigate the unwanted popcorn formation of a cross-linked polymer having internal mechanical strain comprising the steps of:
   a) providing an installation in which unwanted popcorn formation of a cross-linked polymer may occur, with at least one resonant piezo electric transducer being attached outside of the installation;
   b) counting the acoustic emissions generated by the cross-linked polymer formation originating by the sudden break of the polymer with the at least one resonant piezo electric transducer and comparing the number of acoustic emissions counted per unit of time with at least one predefined threshold; and
   c) intervening on the installation in order to limit the unwanted popcorn formation of a cross-linked polymer when the number of acoustic emissions counted per unit of time of step b) is higher than the at least one predefined threshold;
wherein the step of counting the acoustic emissions is done by detecting a second harmonic of the acoustic emissions.

2. The process according to claim 1 wherein the step b) of counting the acoustic emissions includes monitoring the increase of the number of acoustic emissions counted per unit of time.

3. The process according to claim 1 wherein a resonant frequency, V/μbar, calibrated with ASTM E976, of the resonant piezo electric transducer is in the range of 140 to 180 kHz.

4. The process according to claim 1 wherein the resonant piezo electric transducer measures the second harmonic of the acoustic emissions being in the range of 140 to 180 kHz or being in the range of the resonant frequency of the resonant piezo electric transducer.

5. The process according to claim 1 wherein the step b) of counting the acoustic emissions includes filtering and amplifying the signal obtained by the resonant piezo electric transducer during the measurement of the acoustic emissions.

6. The process according to claim 1 wherein the resonant piezo electric transducer has an operating frequency range of at least more than two times the frequency of the second harmonic or has a operating frequency range from 1 to 450 kHz.

7. The process according to claim 1 further comprising the steps performed after step a) of:
   a1) attaching the at least one resonant piezo electric transducer outside the installation
   a2) checking the coupling of the installation with the at least one resonant piezo electric transducer.

8. The process according to claim 1 wherein the resonant piezo electric transducer is permanently attached to the installation and that the counting the acoustic emissions emitted during the unwanted formation of popcorn is performed on a continuous way.

9. The process according to claim 1 wherein the step c) of intervening on the installation includes one or more of the following:
   injecting at least one additive able to limit the formation of unwanted popcorn;
   isolating and washing the part of the installation where unwanted popcorn formation was detected or removing the unwanted popcorn present;
   stopping the installation in order to mechanically or manually remove or washing the unwanted popcorn; or
   locating on the installation where the number the acoustic emission is the maximum and nearby injecting at least one additive able to limit the formation of unwanted popcorn polymers.

10. The process according to claim 9 wherein the additive able to limit unwanted popcorn formation of a cross-linked polymer is chosen among compounds having 2,2,6,6-tetramethylpiperidine group at a concentration of 1 to 5 wt ppm; or phenolic stabilizer being at a concentration of 200 to 1000 wt ppm; or group of molecules being hydroxylamine compounds being at a concentration of 50 to 500 wt ppm; or di-lower akylhydroxylamine or:
   4-Hydroxy-2,2,6,6-tetramethylpiperidine 1-oxyl at a concentration of 1 to 5 wt ppm or
   4-tert-Butylcatechol at a concentration of 200 to 1000 wt ppm or
   di ethyl hydroxylamine at a concentration of 50 to 500 wt ppm or any combination of thereof
and wherein the concentration is based on the total weight of the stream in which the unwanted popcorn formation of cross-linked polymer may occur and is measured at the point of injection of the additive.

11. The process according to claim 1 wherein the unwanted popcorn formation of a cross-linked polymer is derived from 1,3-butadiene, isoprene, dimethyl-2,3-buta-1,3-diene, chloroprene, bromoprene, styrene containing impurities, divinylbenzene and styrene containing traces of divinylbenzene.

12. The process according to claim 1 wherein the resonant piezo electric transducer is connected to a conditioner unit comprising at least one filtering mean and an operational preamplifier and wherein in the conditioner unit there is at least one adjustable threshold level or a plurality of cascaded threshold levels.

13. The process according to claim 10 wherein the injection of at least one additive able to limit the formation of unwanted popcorn polymers is performed when the number of acoustic emissions counted per unit of time reaches the predefined threshold and that the concentration of the additive injected is further increased when the number of acoustic emissions counted per unit of time reaches a second predefined threshold higher than the predefined threshold and that isolating and washing the part of the installation where unwanted popcorn formation was detected or removing the unwanted popcorn present or the stopping the installation in order to mechanically or manually remove or washing the unwanted popcorn is performed when the number of acoustic emissions counted per unit of time reaches a second predefined threshold higher than the first predefined threshold.

14. The process according to claim 1 wherein the step b) of counting the acoustic emissions is performed using multiple resonant piezo electric transducers located where unwanted popcorn formation of a cross-linked polymer may occur.

* * * * *